United States Patent [19]

Chapelon et al.

[11] Patent Number: 5,601,526
[45] Date of Patent: Feb. 11, 1997

[54] ULTRASOUND THERAPY APPARATUS DELIVERING ULTRASOUND WAVES HAVING THERMAL AND CAVITATION EFFECTS

[75] Inventors: Jean-Yves Chapelon, Villeurbanne; Dominique Cathignol, Genas; Albert Gelet, Lyon; Emmanuel Blanc, S. Genis-Laval, all of France

[73] Assignees: Technomed Medical Systems, Bron; Institut National de la Sante et de la Recherche Medicale, Paris, both of France

[21] Appl. No.: 244,953

[22] PCT Filed: Dec. 21, 1992

[86] PCT No.: PCT/FR92/01210

§ 371 Date: Nov. 29, 1994

§ 102(e) Date: Nov. 29, 1994

[87] PCT Pub. No.: WO93/12742

PCT Pub. Date: Jul. 8, 1993

[30] Foreign Application Priority Data

Dec. 20, 1991 [FR] France .................................. 91 15942
Dec. 20, 1991 [FR] France .................................. 91 15943

[51] Int. Cl.$^6$ ...................................................... A61N 7/00
[52] U.S. Cl. ................................. 601/3; 607/97; 601/2; 601/4; 128/660.03
[58] Field of Search ..................... 128/660.03; 601/3–4; 607/97

[56] References Cited

U.S. PATENT DOCUMENTS 2,283,285  7/1945  Pohlman .
2,559,227  3/1951  Rieber .
4,528,979  7/1985  Marchenko et al. .
4,813,402  3/1989  Reichenberger et al. .
4,962,752  10/1990 Reichenberger et al. .
5,143,073  9/1992  Dory ................................. 128/660.03
5,158,070  10/1992 Dory .

FOREIGN PATENT DOCUMENTS 256202  2/1988  European Pat. Off. .
330816  6/1989  European Pat. Off. .
363239  11/1990 European Pat. Off. .
2639238 5/1990  France .
3150513 6/1983  Germany .
4006762 9/1991  Germany .
820814  9/1959  United Kingdom .
2167305 5/1986  United Kingdom ............. A61F 9/00

OTHER PUBLICATIONS

F. Dunn and F. J. Fry Ultrasonic Threshold Dosages for the Mammalian Central Nervous System, IEEE Transaction on Biomedical Engineering, 18:4, 253–256, Jul. 1971.

*Primary Examiner*—Marvin M. Lateef
*Assistant Examiner*—Eleni Mantis Mercader
*Attorney, Agent, or Firm*—Pennie & Edmonds

[57] ABSTRACT

A method and apparatus for performing therapy using ultrasound. The apparatus uses a treatment device having at least one piezoelectric transducer element to supply ultrasonic waves focussed onto a focal point or region that determines the tissue zone submitted to therapy. The treatment device, which is controlled by a control device, supplies two types of ultrasonic waves, the first one being thermal waves that produce a predominantly thermal effect on the tissue being treated and the second one being cavitation waves that produce a predominantly cavitation effect on the tissue to be treated.

40 Claims, 7 Drawing Sheets

ULTRASOUND THERAPY APPARATUS DELIVERING ULTRASOUND WAVES HAVING THERMAL AND CAVITATION EFFECTS

BACKGROUND OF THE INVENTION

The present invention essentially relates to an ultrasound therapy apparatus which delivers ultrasound waves that produce thermal and cavitation effects.

The present invention also relates to therapy apparatus employing ultrasound, fitted with a cooling device.

It is known that a high-power focused ultrasound acoustic field is able to destroy human body tissue (see PCT published applications in the name of Fry W0-89/07907 and W0-98/07909).

Dunn and Fry have also described in "Ultrasonic threshold dosage for the mammalian central nervous system" IEEE transactions, volume BME 18, pages 253–256 how this destruction process involves two effects, more specifically a thermal effect and a cavitation effect.

The thermal effect predominates when the acoustic power at the point of focus is below a determined threshold of about 150 W/cm$^2$ at 1 MHz. This thermal effect is due to the acoustic absorption of the tissue, which converts the mechanical energy of the acoustic wave into thermal energy.

The cavitation effect becomes predominant when the acoustic power at the point of focus exceeds a threshold of 150 W/cm$^2$. This cavitation effect is linked to the formation of microscopic bubbles of gas which explode when they reach a critical diameter with local release of appreciable amounts of energy leading to destruction of neighbouring tissue.

In order to obtain destruction of tissue exclusively by thermal effects, it is necessary for the acoustic field to be able to reach a threshold of destruction referred to as the "thermal dose". This threshold is a function of temperature reached and of the duration of application. It is thus possible to destroy tissue by application of a moderate temperature increase over a long duration of application or, on the contrary, through application of a significant temperature increase over a short period of application.

The temperature increase is directly linked to the acoustic power of the ultrasound field at the point of focus.

In the case of a moderate temperature and a long duration of application, transfer and spreading of heat energy occurs around the point of focus, notably due to thermal conduction in the medium and to blood flow, which leads to poor control of the volume being treated, which may lead to healthy zones being destroyed with a resultant impairment of the quality of treatment.

In the case of elevated temperature and a short duration of application, the acoustic power at the focal point exceeds the abovesaid cavitation threshold, with the resultant obtaining of cavitation effects having a significant destructive power. This cavitation effect is particularly important at the various interfaces that the acoustic field encounters, for example at the skin, the muscles and the walls of organs. This leads to poor mastery of tissue destruction, as the latter is not limited to the zone immediately around the focus of the transducer.

SUMMARY OF THE INVENTION

The present invention thus sets out to resolve the new technical problem, which is that of supplying a solution allowing a lesion in tissue to be treated which is strictly limited to the focal point of the treatment device comprising at least one piezoelectric transducer element, and limiting or avoiding effects due to heat spreading around the focus point, with cavitation phenomena being limited exclusively to the focal point or to the focal region, and without substantial cavitation phenomena being produced outside said focal point or region.

A further aim of the invention is to resolve the new technical problem by providing a solution which enables a tissue lesion to be treated which is strictly limited to the focal point of the treatment device comprising at least one piezoelectric transducer element, at the same time allowing a point-by-point treatment of the complete tissue area of the target requiring treatment to be obtained, such as for example benign and malignant tumors well known to those skilled in the art, regardless of whether they be external or internal. Presently preferred applications are the treatment of benign and malignant tumors of the liver, the prostate, the kidney, the breast, the skin, the brain and the treatment of varicose effects and of the esophagus.

Yet a further aim of the present invention is to resolve the new technical problem consisting in supplying a solution enabling the temperature of tissue which needs to be protected to be controlled in order to limit cavitation effects encountered for high acoustic energy levels, such as those required in the performance of therapy, in particular at the various interfaces and above all at the interface defined by the skin of a mammal to be treated, in particular a human being.

All these technical problems are resolved for the first time by the present invention in a manner which is simultaneously simple, reliable, inexpensive, and capable of use on an industrial and medical scale.

Thus, according to a first aspect, the present invention provides an apparatus for performing therapy using ultrasound, comprising at least one treatment device comprising at least one piezoelectric transducer element designed to provide at least said therapy for the purpose of treating a target to be treated such as tissue which may be located inside the body of a mammal, in particular a human being, and control means for said device in order to carry out said therapy, said piezoelectric transducer element being designed to supply ultrasonic waves focused onto a focal point or region determining the tissue zone to be submitted to said therapy, characterized in that it comprises control means for said device designed to cause said treatment device to supply ultrasonic waves of two types, the first type, referred to herein as thermal waves, producing a predominantly thermal effect on the tissues to be treated, and a second type referred to herein as cavitation waves producing a predominantly cavitation effect on said tissues to be treated.

In accordance with one advantageous embodiment, the said control means control within said treatment device, at least at the beginning of said treatment, thermal ultrasonic waves.

In accordance with an advantageous embodiment, the said control means for the treatment device control the transmission of cavitation ultrasonic waves after an adjustable predetermined time interval allowing pre-heating of the tissue to be treated to be obtained.

In accordance with one special embodiment, the said control means enable the transmission of cavitation ultrasonic waves to be controlled simultaneously with the transmission of thermal ultrasonic waves, in particular after the abovesaid time interval during which only thermal ultrasound waves are transmitted.

In accordance with another particular embodiment, the acoustic power of the thermal ultrasonic waves is lower than the cavitation threshold whereas the acoustic power of the cavitation ultrasonic waves is at least equal to the cavitation threshold, said cavitation threshold being a function of the tissue of the mammal to be treated.

In accordance with another embodiment of the invention, the frequency of said cavitation ultrasonic waves is lower than the frequency of said thermal ultrasonic waves.

In accordance with one embodiment the control means provide for transmission of cavitation ultrasound waves including a negative component of amplitude of a nature to initiate cavitation.

In accordance with another embodiment the said control means provide the transmission of cavitation ultrasound waves for a duration comprised between about 0.5 microseconds and about 100 milliseconds, and preferably comprised between 0.5 microseconds and 50 microseconds.

In accordance with yet another particular embodiment the said control means provide transmission of cavitation ultrasound waves by successive pulses, the repetition frequency of which varies from about 1 Hz to 1 KHz, preferably from about 10 Hz to 100 Hz.

In accordance with one particular embodiment the duration of said adjustable predetermined time interval is comprised between about 100 milliseconds and about 10 seconds.

In accordance with yet a further embodiment the total duration of treatment of the tissue region determined by the focal point or region by means of the said ultrasound waves is comprised between 100 milliseconds and 10 seconds, this total duration including at least one pulse of cavitation ultrasound waves.

In accordance with yet a further particularly advantageous embodiment, the apparatus is characterized in that it comprises means for displacing said treatment device in order to perform point-by-point treatment, each of said points being determined by the said focal point or region, in order to cover the whole volume of the target to be treated.

Preferably, the said displacement means of the treatment device are controlled by a central control unit, comprising for example calculating means such a computer or a microcomputer, the latter being preferably provided with software managing the displacement of said treatment device as a function of the volume of the target to be treated, volume data having advantageously been acquired by imaging means associated therewith.

In accordance with yet a further embodiment, the control unit controls the displacement of said displacing means of said treatment device in order to carry out treatment of the tissue regions of the target which are most remote from said treatment device up to the tissue regions that are closest to said treatment device in order to improve the effectiveness of treatment of said target. The invention resolves the problem of treating remote zones, by treating them first so that necrosis of close zones does not stand in the way of treatment of zones that are more remote.

In accordance with yet a further advantageous embodiment, the control means provide a latency period between the treatment of two successive points on the target to be treated in order to allow said tissue being treated to relax, said latency period being preferably comprised between about 1 second and 15 seconds, said latency period being advantageously employed for carrying out the displacement of the treatment device from one treatment point to another.

In accordance with a further embodiment, the control unit controls a displacement of said displacement means of said treatment device in a random manner while nevertheless excluding points that have already been treated.

In accordance with yet a further embodiment, the frequency of transmission of said cavitation ultrasound waves is comprised between about 500 KHz and 4 MHz, preferably between 500 KHz and 2 MHz, and even more preferably is about 1 MHz.

In accordance with one embodiment, the frequency of transmission of said thermal ultrasound waves is comprised between about 1 and 4 MHz, said frequency being at least equal to the frequency of said cavitation ultrasound waves.

In accordance with yet a further embodiment, the acoustic power of said thermal ultrasound waves is lower than about 150 W/cm$^2$, and the acoustic power of said cavitation ultrasound waves is at least equal to about 150 W/cm$^2$.

In accordance with an advantageous embodiment, the said control means provide transmission of ultrasound waves of an amplitude that varies as a function of time, said amplitude preferably increasing with the passage of time, whereby the amplitude over a first period remains below a cavitation threshold, then, in a second period becomes higher than said cavitation threshold.

From a second independently patentable aspect, the invention provides apparatus for therapy by ultrasound, comprising at least one treatment device designed to provide at least said therapy for the purpose of destroying a target to be destroyed such as tissue which may be located inside the body of a mammal, in particular a human being, and control means for said device in order to carry out said therapy, said piezoelectric transducer element being designed to supply ultrasonic high energy acoustic waves focused onto a focal point or region determining the tissue zone to be submitted to said therapy, said ultrasound waves passing through tissue regions located at the interface with said therapy apparatus, characterized in that it comprises cooling means allowing refrigeration or cooling to be performed in a predetermined temperature range, of at least the tissue regions located at the interface with said therapy apparatus allowing the tissue regions located at said interface to be efficiently protected against cavitation effects.

In an advantageous embodiment, the cooling means comprise a refrigerating fluid, preferably an aqueous cooling medium such as water.

In a particularly advantageous embodiment, the therapy apparatus including said at least one piezoelectric transducer element is provided with a membrane forming a sealed watertight cavity between said membrane and said piezoelectric transducer element, completely filled with cooling fluid, means for circulating said cooling fluid being also provided in order to ensure renewal and to keep it within the desired temperature range.

In one embodiment, the said cooling means also cool said piezoelectric transducer element.

In another embodiment, a cooling fluid temperature regulating device is provided, which for example includes one or several temperature sensors well known in the art.

In accordance with yet a further embodiment, the therapy apparatus is extracorporeal.

In accordance with yet a further embodiment said therapy device is an endo-cavitary device allowing therapy by semi-invasive treatment to be achieved, said endo-cavitary device being in particular an endo-rectal or endo-urethral or even an endo-esophagal device.

In an advantageous embodiment, the temperature of the cooling fluid is lower than the mammal's body temperature, and in particular is below 37° C., and even better below 35° C., and better still below 30° C.

A particularly useful range of temperatures is that comprised between 4° C. and 30° C., and even better between 15° C. and 25° C.

In accordance with a particular embodiment, there is included at least one endo-cavitary device physically independent of said therapy device for cooling tissue regions remote from said therapy device and which it is also desired to protect during said therapy. The endocavitary device is advantageously fed with the same cooling fluid as the therapy apparatus.

In accordance with yet a further independently patentable embodiment, provision is made for at least one temperature measuring device for the tissue located at the interface with said therapy device, and for means for receiving and transmitting temperature data transmitted by the temperature measuring device to a control unit capable of modifying the instructions controlling the operation of said therapy apparatus as a function of the temperature data received. Preferably, the temperature measuring devices comprise sensors in the form of a thermocouple or in sheet-form, particularly of the PVDF type which has the advantage of being able to be provided in extremely thin film form, and which can thus be disposed directly on the tissue regions of the interface, opposite the therapy device, or yet again, on the outer side of the membrane enclosing the cooling fluid, said membrane being applied against the surface of the interface tissue. Moreover, here, the sensor which is advantageously in sheet form, particularly PVDF-sheet form enables measurement of the ultrasound acoustic pressure field delivered by the therapy device to be measured at interface level, this making it possible to know, with considerable accuracy and moreover in real time, what the acoustic power in the focal region is, enabling the electrical power supplied to the transducer element to be regulated for keeping the ultrasonic acoustic field pressure at a constant value at focal point F.

The therapy apparatus can be used with, or applied to, all types of therapy by ultrasound, preferably focused, of all benign or malignant external or internal tumors, and preferably for the treatment of benign and malignant tumors known to those skilled in the art, whether such tumors be internal or external. Preferred current applications are the treatment of benign or malignant tumors of the liver, of the prostate, of the kidney, of the breast, of the skin, of the brain and for the treatment of varicose states and of the esophagus. The invention also covers the use or application of such a therapy apparatus for manufacturing equipment for treating benign or malignant tumors.

The invention also covers a therapeutic treatment method which results clearly from the preceding description of the apparatus, as well as the embodiments of currently preferred devices which will now be described in detail with reference to the attached drawings which constitute an integral part of the invention and in consequence an integral part of this present specification.

The invention enables thermal treatment of tissue to be combined with treatment by cavitation, perfect spatial mastery thereof being maintained. The combination of cavitation and thermal treatment has the effect of reinforcing the destructive potential of treatment, and hence limiting the duration of treatment pulses and thus avoiding heat energy spreading within the tissue.

In the case of a therapeutic treatment extended to lesions having a volume greater than that of the focal spot, the sequences of treatment pulses previously described are carried out point-by-point by displacing the focal point using associated mechanical or electronic control means, between each shot, in order that the focal volume can describe the total volume of the lesion.

Similarly, the invention enables a particularly effective cooling of the tissue located in the interface region with the therapy device to be obtained, also ensuring cooling of the piezoelectric transducer elements of the therapy device, and, in an unexpected manner, the invention enables the cavitation effects on tissue at the interface region and, also, in the coupling, here constituted by the cooling fluid, to be reduced.

This is moreover achieved in an extremely simple manner since it is possible to use ordinary tap water, which preferably is degassed, as the latter is circulating in a closed circuit and is never in contact with the patient, its temperature being able to be controlled in an extremely simple manner using all temperature regulation devices well known to those skilled in the art. Additionally, the water which is present also has the advantage of only absorbing very slightly the ultrasound and, consequently, not becoming heated under the action of the ultrasound field, thus preserving its cooling capacity.

Another unexpected effect resulting from the limitation of the cavitation effects resides in the fact that it is possible to increase the power of the acoustic waves and thus to limit the duration of treatment, which furthermore enables the effects of heating up the tissue, notably by spread of heat, to be limited.

BRIEF DESCRIPTION OF THE DRAWINGS

Other aims, features and advantages of the invention will become more clear from the description which follows with reference to the attached drawings which illustrate three currently preferred embodiments of the invention, provided simply by way of illustration and which should not be considered as limiting in any way the scope of the invention. In the figures.

DETAILED DESCRIPTION OF THE PREFERRED EMBODIMENTS

Figure 1:
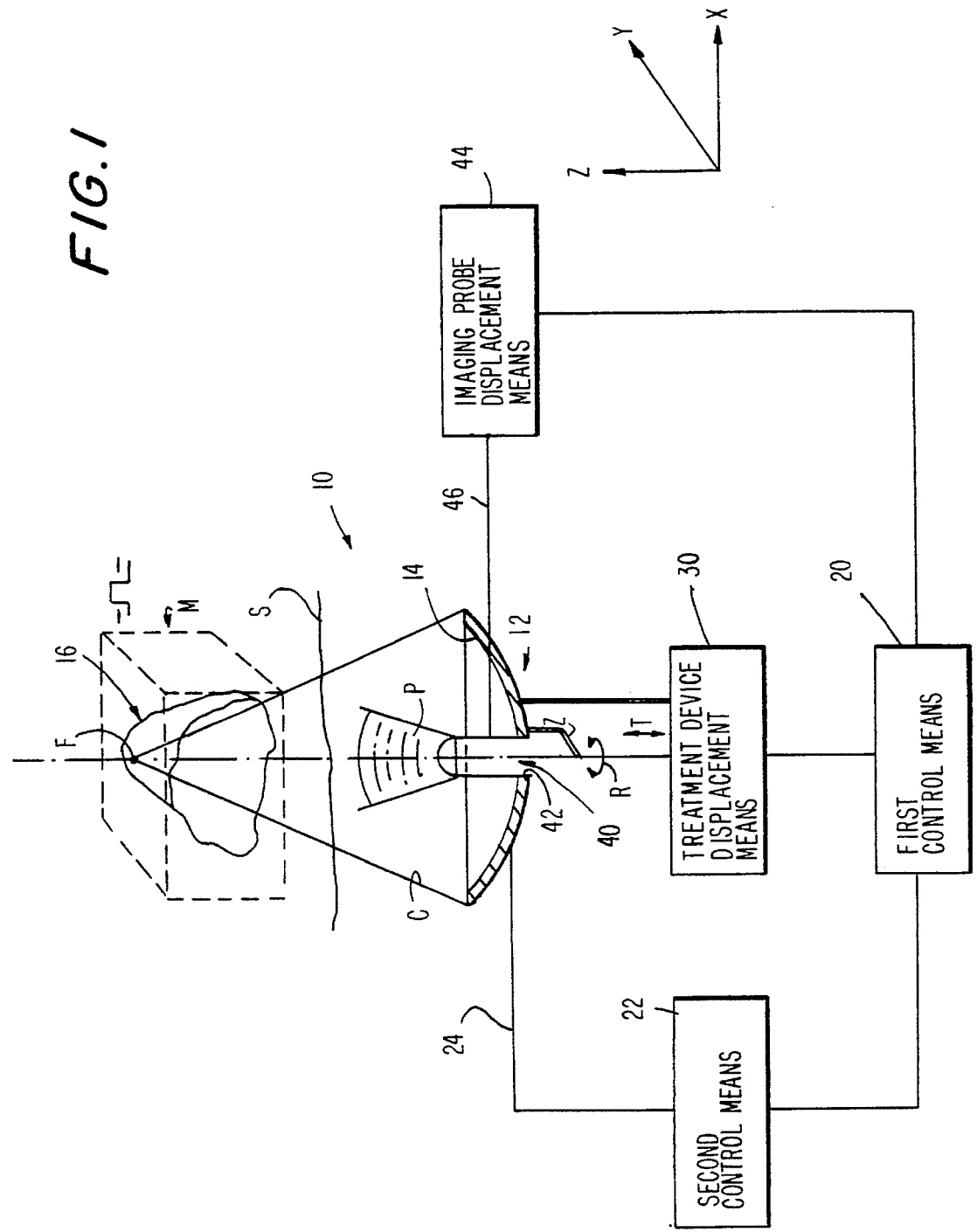
FIG. 1 is a diagram showing the essential components of an ultrasound therapy apparatus according to the present invention.

Referring now to FIG. 1, an extracorporeal therapy device according to the invention is illustrated identified by the general reference number 10. This apparatus comprises at least one extracorporeal treatment device bearing the general reference number 12 comprising at least one piezoelectric transducer element 14 designed to provide at least said therapy for the purposes of treating a target to be treated, such as tissue, shown diagrammatically by general reference number 16, which may be situated inside the body of a mammal M, in particular a human being. The skin surface of this mammal is identified by the letter S. This apparatus further comprises control means such as 20, 22 controlling the device 12, as is shown symbolically by the link 24. The piezoelectric transducer element 14 is preferably designed to deliver ultrasonic waves focused onto a focal point or zone F, the focused acoustic field being shown symbolically by the letter C. The point of focal zone F obviously determines the tissue region which is to be subjected to said therapy.

The apparatus is characterized in that it comprises control means 20, 22 for said treatment device 12 designed to cause said treatment device 12 to supply ultrasonic waves of two types, the first type, referred to herein as thermal waves, producing a predominantly thermal effect on the tissues 16 to be treated, and a second type referred to herein as cavitation waves producing a predominantly cavitation effect on said tissues to be treated.

In an advantageous embodiment, the said control means 20, 22 control, within said treatment device 12, at least at the beginning of said treatment, thermal ultrasonic waves.

In another advantageous embodiment, the said control means for the treatment device control the transmission of cavitation ultrasonic waves after an adjustable predetermined time interval allowing pre-heating of the tissue to be treated. The said control means advantageously enable the transmission of cavitation ultrasonic waves to be controlled simultaneously with the transmission of thermal ultrasonic waves, and in particular after the abovesaid time interval during which only thermal ultrasound waves are delivered.

Figure 2:
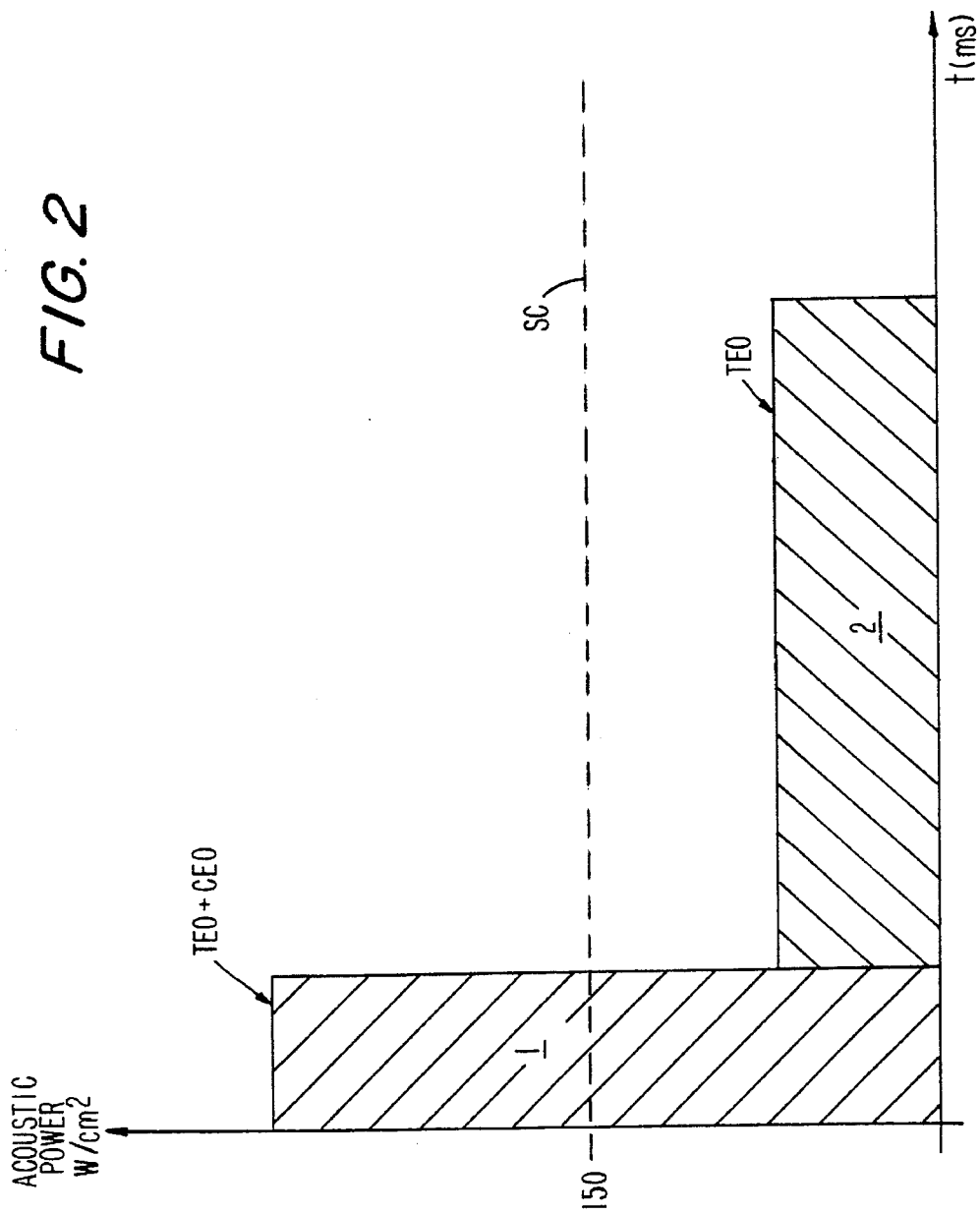
FIG. 2 shows the threshold of the cavitation effects and the areas of thermal effects alone, or of thermal effects plus cavitation effects, as a function of acoustic power on the y axis expressed in Watts per centimeter squared, as a function of time on the x axis, expressed in milliseconds.

In another embodiment, the acoustic power of said thermal ultrasonic waves is lower than the cavitation threshold at focal point F shown in dash-dot lines in FIG. 2 and bearing the reference SC, whereas the acoustic power of said cavitation ultrasonic waves is at least equal to the cavitation threshold SC at focal point F, said cavitation threshold SC at focal point F being a function of the tissue of the mammal to be treated.

In another embodiment, the frequency of said cavitation ultrasonic waves sent by transducer element 14 under control of control means 20, 22 is lower than the frequency of first and second said thermal ultrasonic waves.

In a further embodiment, said control means provide for transmission of cavitation ultrasound waves including a negative component of the amplitude thereof of a nature to initiate cavitation.

In a further embodiment, the acoustic power of first and second said thermal ultrasound waves is lower than about 150 W/cm$^2$, and the acoustic power of said cavitation ultrasound waves is at least equal to about 150 W/cm$^2$. The value of 150 W/cm$^2$ as shown in FIG. 2, represents the cavitation threshold at focus point F of the tissue of a cancerous tumor of the body of a mammal, in particular a human being. In FIG. 2, a region 1 of acoustic power has been shown for which the ultrasound waves have an acoustic power which extends beyond this cavitation threshold. These ultrasound waves hence exhibit a combination of thermal effect acoustic waves (TEO) and predominantly cavitation-effect ultrasonic waves (CEO). In contrast, in region 2, the acoustic power of the ultrasound waves is well below this cavitation threshold, the ultrasound waves being only thermal-effect ultrasonic waves as can be readily understood from FIG. 2.

In one particular embodiment, the frequency of said cavitation ultrasonic waves is lower than the frequency of said thermal ultrasonic waves.

In another embodiment, the control means provide for transmission of cavitation ultrasound waves including a negative component of the amplitude thereof of a nature to initiate cavitation.

In another embodiment, the said control means 20, 22 provide the transmission of cavitation ultrasound waves for a duration comprised between about 0.5 microseconds and about 100 milliseconds, and preferably comprised between 0.5 microseconds and 50 microseconds.

In yet another embodiment, the said control means 20, 22 provide transmission of cavitation ultrasound waves by successive pulses, the repetition frequency of which varies from about 1 Hz to 1 KHz, preferably from about 10 Hz to 100 Hz.

In another embodiment, the duration of said adjustable predetermined time interval is comprised between about 100 milliseconds and about 10 seconds.

The total duration of treatment, in one embodiment, of the tissue region determined by the focal point or region F by means of the said ultrasound waves is comprised between 100 milliseconds and 10 seconds, this total duration including at least one pulse of cavitation ultrasound waves.

In another embodiment, the apparatus is characterized in that it comprises means 30 for displacing said treatment device 12 in order to perform point-by-point treatment, each of said points being determined by the said focal point or region F, in order to cover the whole volume of the target 16 to be treated.

Preferably, the said displacement means 30 of the treatment device 12 are controlled by a control means 20, comprising for example calculating means such a computer or a micro-computer, the latter being preferably provided with software managing the displacement of said treatment device 12 by suitable control of the displacement means 30 along the three coordinates X, Y and Z as a function of the volume of the target to be treated.

Advantageously, an imaging device such as ultrasonographic imaging means, bearing the general reference 40 and disposed in a central opening 42 of treatment device 12 are provided, said imaging device 40 being preferably coaxial with focused treatment device 12 so that the focal point or region F can be monitored permanently. Imaging device 40, as is well known is mounted so as to be advantageously rotatable about its common axis identified by arrows R and/or in translation along a common axis identified by arrow T, through imaging probe displacement 44 with a link 46. The imaging device preferably employs a commercially available ultrasonographic probe using type B ultrasonography, in other words sweeping a plane shown in FIG. 1 and bearing reference P. Imaging device 40 enables volume data to be obtained on the target 16 to be treated, for transmission to control means 20 for processing by the latter's software. Control means 20 controls, by unit 30, the displacements of treatment device 12 as well as the means 44 for displacing the imaging probe 40, in rotation and/or in translation.

In a particular embodiment, the control means 20 controls the displacement of said displacing means 30 of said treatment device 12 and/or the imaging probe associated therewith, in other words integrally with the displacement of the treatment device 12, in order to carry out treatment of the tissue regions of said target which are most remote from said treatment device 12, as shown in FIG. 1, up to the tissue regions that are closest to said treatment device 12 in order to improve the effectiveness of treatment of said target 16.

In accordance with an advantageous embodiment, the control means 20 controls a displacement of said displacement means 30 of said treatment device 12 in a random manner while nevertheless excluding points that have already been treated.

In an advantageous embodiment, the control means 22 provide a latency period between the treatment of two successive points on the target to be treated in order to allow said tissue being treated to relax, said latency period being preferably comprised between about 1 second and 15 seconds, said latency period being advantageously employed for carrying out the displacement of the treatment device 12 from one treatment point to another, by controlling the displacement means 30 from the control unit. In particular, with reference to FIG. 7, the point-by-point treatment sequence has been illustrated. For example, treatment of the first point in the first focal region is indicated by F1 and the duration of treatment by $t_{F1}$, the period of latency following this is identified by $t_{L1}$, whereby the total treatment time from the point formed by the focal region F1 is t (total for F1). For the following point, point 2, formed by focal region F2, which is different from F1, and which is determined by control unit 20, the treatment time for this point F2 is identified by $t_{F2}$, the latency period is identified by $t_{L2}$ and total treatment time is t (total for F2), and so on for the other points.

In accordance with an advantageous further embodiment, the frequency of transmission of said cavitation ultrasound waves is comprised between about 500 KHz and 4 MHz, preferably between 500 KHz and 2 MHz, and even more preferably is about 1 MHz.

In accordance with one embodiment, the frequency of transmission of said thermal ultrasound waves is comprised between about 2 and 4 MHz, said frequency being at least equal to the frequency of said cavitation ultrasound waves.

It can thus be seen that the therapy apparatus can be used with, or applied to, all types of therapy by ultrasound, preferably focused, of all benign or malignant tumors, whether such tumors be internal or external. Preferred current applications are the treatment of benign or malignant tumors of the liver, of the prostate, of the kidney, of the breast, of the skin, of the brain and for the treatment of varicose states and of the esophagus. The invention also covers the use or application of such a therapy apparatus as described and illustrated in the drawings which constitute an integral part of the invention and in consequence, of the specification, for manufacturing equipment for treating benign or malignant tumors.

Figure 3:
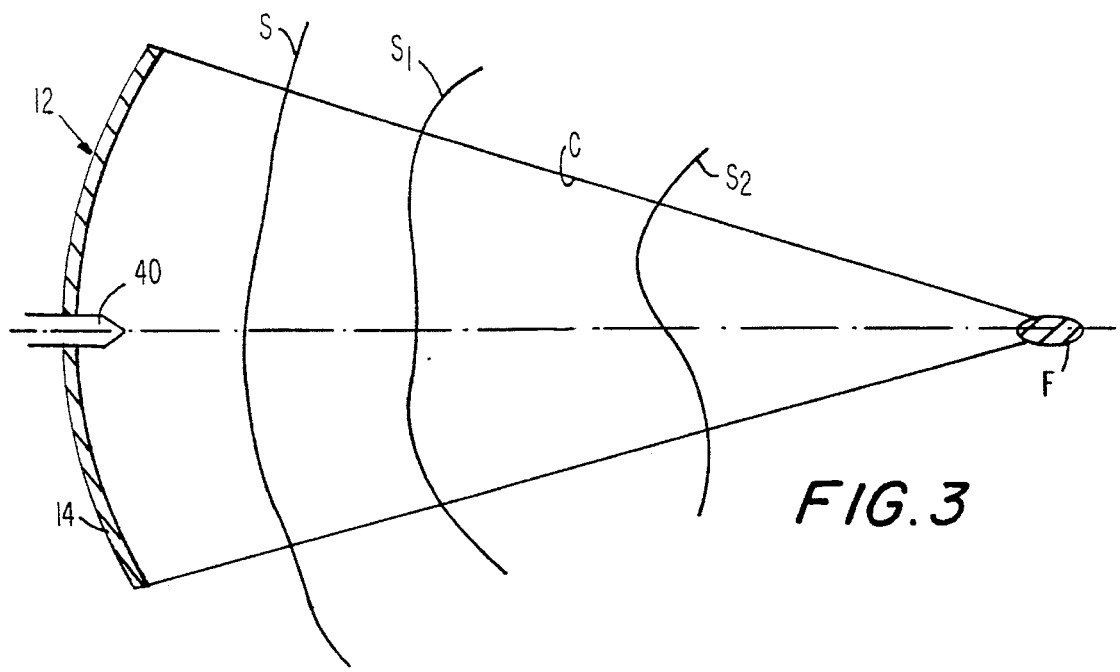
FIG. 3 is a diagrammatical representation of the principle of destruction of tissue structures by reduction of the cavitation threshold, with the treatment device shown in FIG. 1, several interfaces being identified.

With reference to FIG. 3, the various interfaces (such as the patient's skin S, internal interfaces of the patient S1 and S2) are indicated together with the focal region F. The treatment device in FIG. 1 bear the reference 12, the piezoelectric transducer element being identified by reference 14, reference 40 indicating the imaging device.

Figure 4:
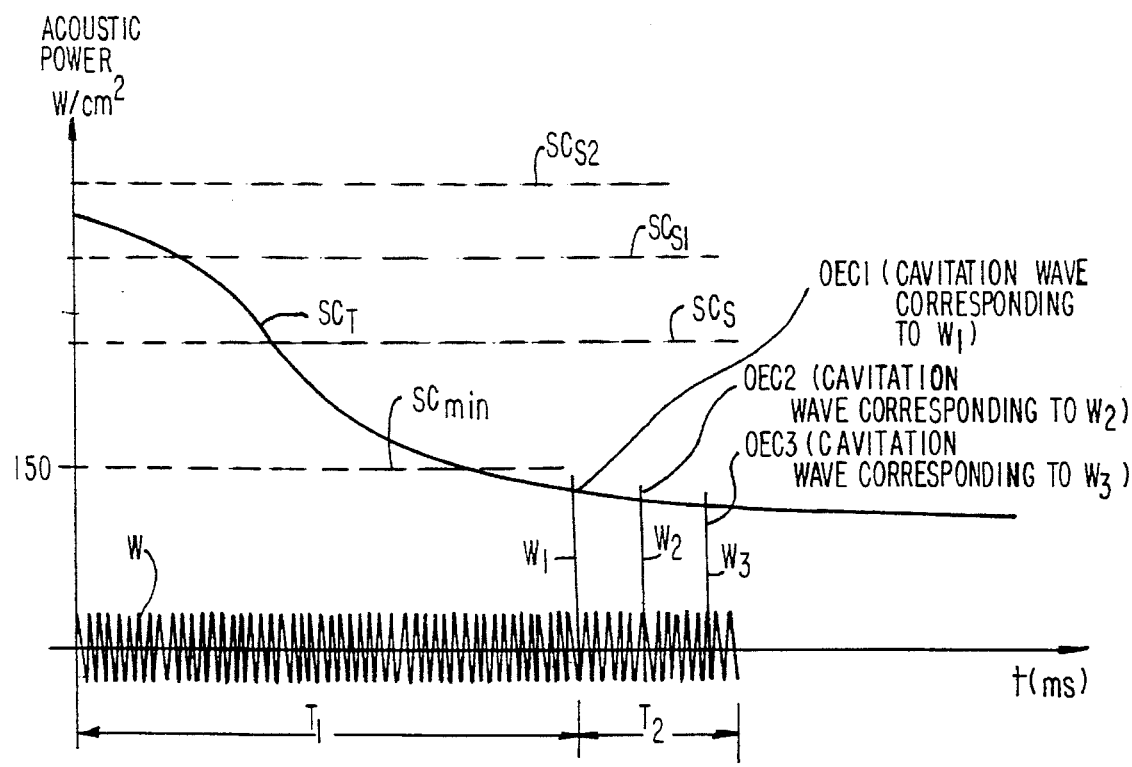
FIG. 4 shows a curve showing how the cavitation threshold varies as a function of acoustic power along the y axis, expressed in Watts per centimeter squared, versus time on the x axis expressed in milliseconds, the cavitation thresholds for the interfaces in FIG. 3 being indicated.

With reference to FIG. 4, the dashed lines show, respectively, the minimum cavitation threshold $SC_{min}$ at 150 W/cm², the cavitation threshold at interface S, $SC_S$, the cavitation threshold at interface S1, $SC_{S1}$, and the cavitation threshold at interface S2, $SC_{S2}$, at ambient temperature.

Curve $SC_T$ shows the curve for the cavitation threshold at the focal point as a function of time, and as a function of the temperature of the tissue. Under the effect of temperature increase of the tissue at focal point F, the cavitation threshold at focal point $SC_T$ diminishes and falls below the thresholds for cavitation $SC_S$ and $SC_{min}$. W indicates the electric control signal supplied by the control means 22 to transducer element 14 over time, the amplitude of which enables predominantly thermal-effect ultrasound waves to be supplied, and electric signals W1, W2 and W3 of short duration of several microseconds up to several milliseconds supplied to transducer element 14, allowing this latter to supply predominantly cavitation-effect ultrasound waves the power of which extends beyond the cavitation threshold SC at the focal point at the instant they are output, as can be seen on FIG. 4. These predominantly cavitation-effect ultrasound waves can be superimposed on W waves, as shown.

It can be noted that the cavitation waves bearing the references OEC1, OEC2, OEC3 corresponding to the signals W1, W2, W3 are only output after a predetermined time interval $T_1$ during which the signals W allow the predominantly thermal-effect waves to be supplied to perform pre-heating of the tissue of the focal region F in order to lower the cavitation threshold at focal point F in a significant manner. This also constitutes one particular preferred technical characteristic, of the present invention.

Figure 7:
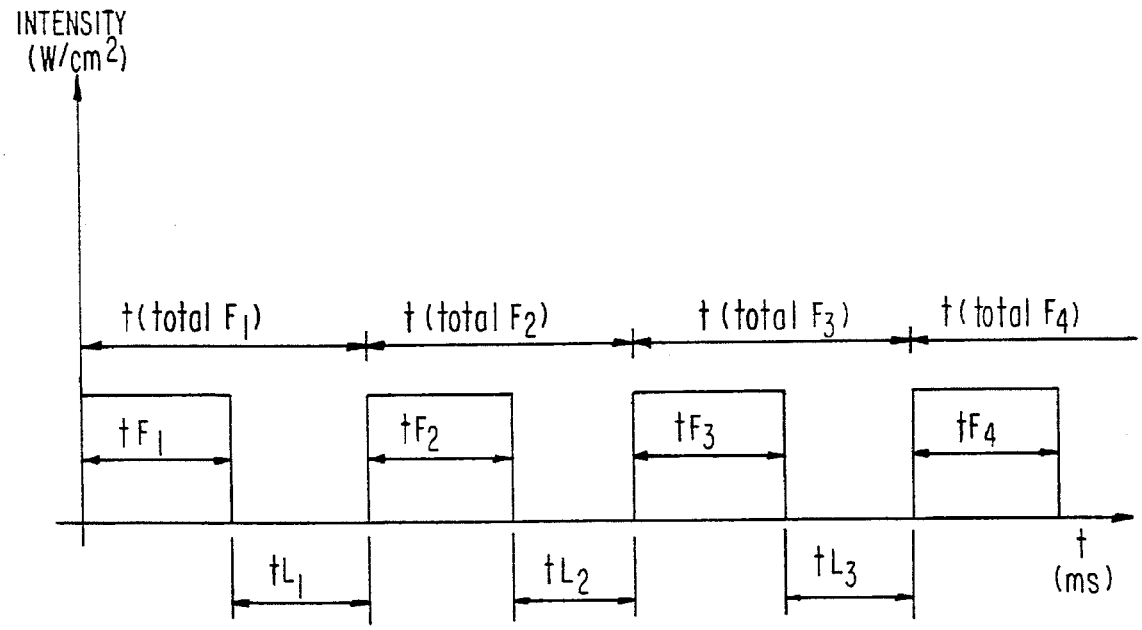
FIG. 7 is a diagrammatic representation showing the frequency of point-by-point treatment, the duration of treatment at each point being indicated.

Period $T_2$ corresponds to the period during which cavitation ultrasound waves are output. As already mentioned previously, the frequency of transmission of cavitation ultrasound waves is comprised between about 500 KHz and 4 MHz, preferably between about 500 KHz and 2 MHz, and better still about 1 MHz, the transmission frequency of the thermal ultrasound waves being about 1 to 4 MHz, this frequency being at least equal to the frequency of the cavitation ultrasound waves. The duration, moreover, of the cavitation ultrasound waves is comprised between about 0.5 microseconds and about 100 milliseconds, and preferably comprised between 0.5 microseconds and 50 microseconds. Moreover, as can be seen in FIG. 7, between the various treatment point $F_1$, $F_2$, $F_3$, $F_4$, a latency period which is preferably comprised between about 1 second and 15 seconds can be seen, said latency period being advantageously employed for carrying out the displacement of treatment device 12 from one point to another, as well as for operation of the imaging control means 44 via a link 46 to imaging means 40.

Figure 5:
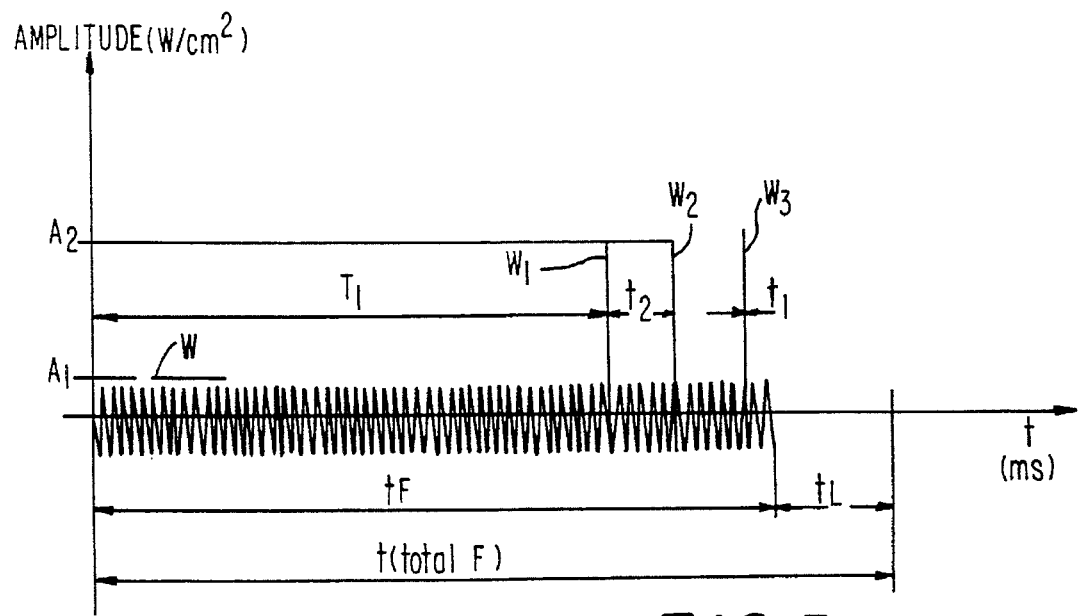
FIG. 5 shows the thermal ultrasound wave curves and the cavitation ultrasound waves as a function of pulse amplitude on the y axis, as a function of time on the x axis expressed in milliseconds.

In FIG. 5, the maximum amplitude $A_1$ of the predominantly thermal-effect ultrasound waves (corresponding to electric signal W) together with the maximum amplitude $A_2$ of the predominantly cavitation-effect ultrasound waves (corresponding to electric signals $W_1$, $W_2$, $W_3$) have been shown. The period of time $T_1$ during which the cavitation ultrasound waves are not issued has also been shown, this period advantageously extending over 100 milliseconds to 10 seconds, the duration of treatment of a point in the focal region F, $t_F$, also being shown together with the time $t_1$ which represents the duration of each cavitation ultrasound wave pulse together with the time $t_2$ between two successive transmissions of cavitation waves, determining the repetition rate of the cavitation pulses. The end of treatment is eventually accomplished from latency period $t_L$.

We have thus determined the total treatment time for point F, which is t (total for F). Thus, referring now to FIG. 7, this data for the treatment of the first point can be found, bearing subscript 1. For point 4, for example, the relevant data bear the subscript 4, and so on.

Figure 6:
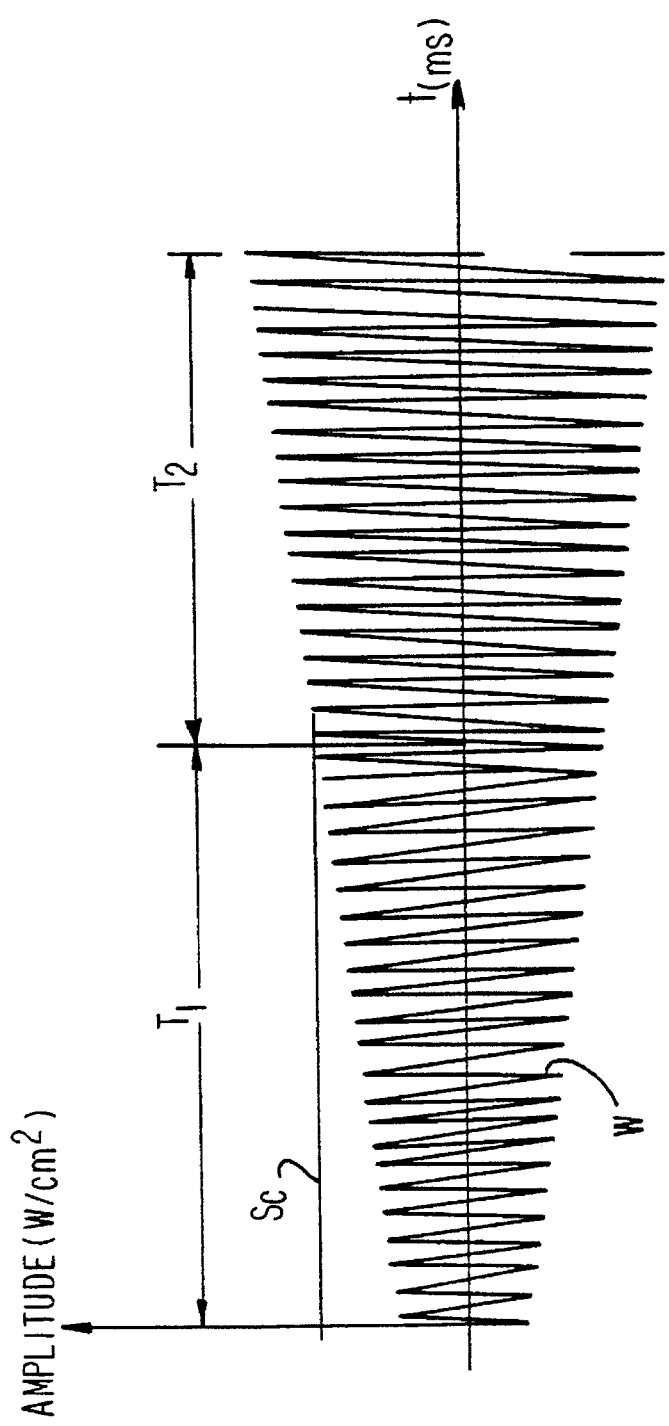
FIG. 6 shows another embodiment of the ultrasound waves the amplitude of which increases with the passage of time in order to provide a first period for which this amplitude is less than the cavitation threshold followed by a second period where said amplitude is higher than said cavitation threshold.

Finally, in FIG. 6, another embodiment has been shown in which control means 20, 22 provide transmission of ultrasound waves the amplitude of which varies as a function of time, and preferably where the said amplitude increases with the passage of time, so that the amplitude during a first period $T_1$ is below a cavitation threshold SC, and then becomes higher than the cavitation threshold SC during a second period $T_2$.

Figure 8:
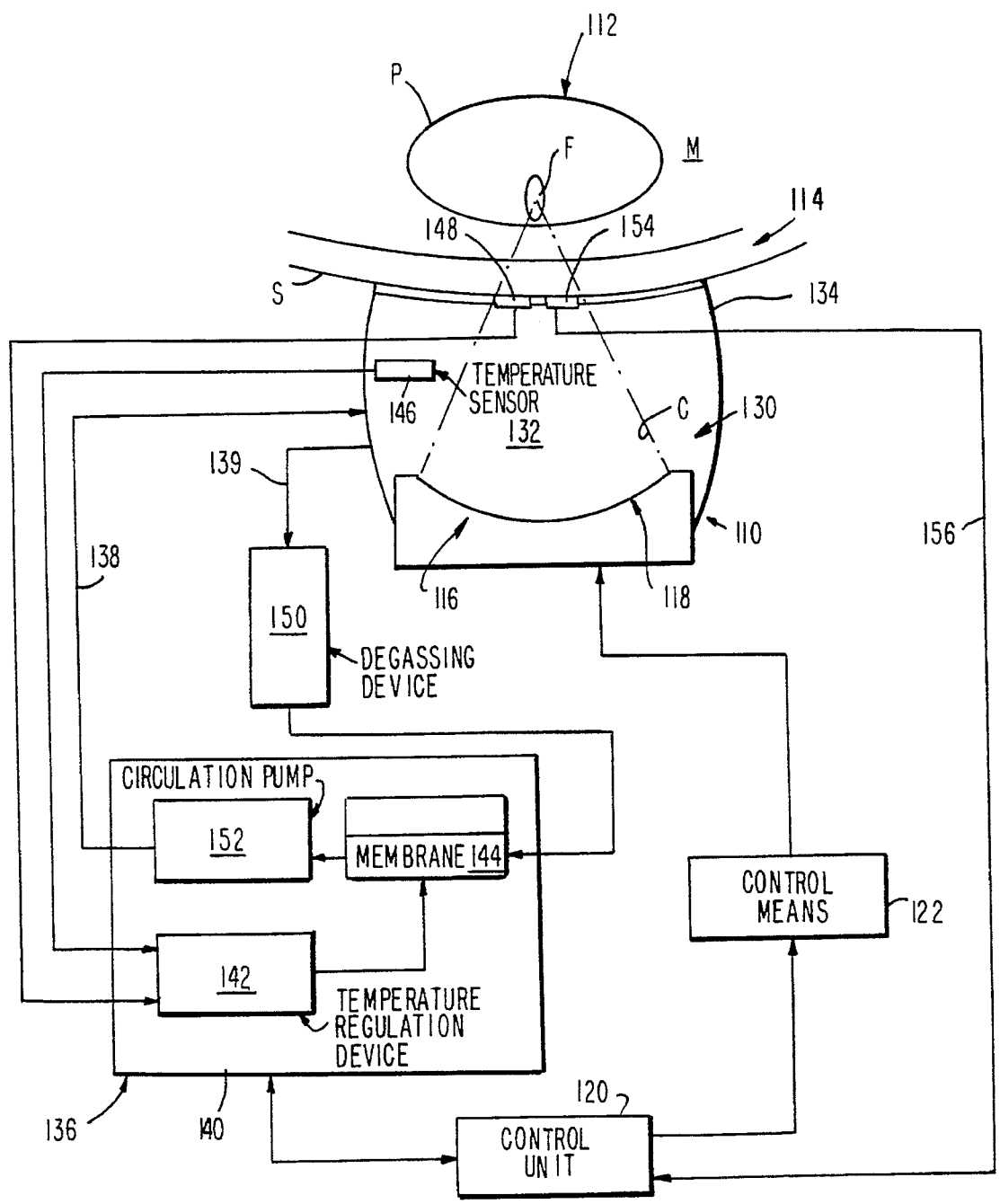
FIG. 8 is a block diagram of an extracorporeal therapy apparatus according to the present invention including means for cooling tissue situated at the interface with the therapy device.

Referring now to FIG. 8, an independently-patentable alternative embodiment, which can optionally be combined with the one illustrated in FIGS. 1 to 7 of a therapy apparatus according to the present invention generally identified reference 110 has been shown diagrammatically. The tissue to be treated is identified by the general reference 112, and the interface zone which notably comprises the interface tissue that is to be preserved is identified by general reference 114. The interface tissue which it is particularly important to preserve is, for example, the skin of a mammal, and preferably of human being.

The therapy apparatus according to the present invention 110 comprises at least one treatment device 116 comprising at least one piezoelectric transducer element 118 designed to provide at least said therapy for the purpose of destroying a target to be destroyed such as tissue 112 which may be located inside the body of a mammal M, in particular a human being. The piezoelectric transducer element 118 is designed to supply focused ultrasound doses at a focal point or region F determining the tissue region to be subjected to said therapy, the focusing field of the ultrasound waves being indicated schematically by reference C.

Control means such as 120, 122 for treatment device 116 for achieving therapy are also provided. The control means preferably comprise a control unit 120, comprising for example calculating means such a computer or a microcomputer, and mechanical and/or electronic control means 122 for treatment device 116, and hence for the piezoelectric transducer elements 118, as well known in the art.

In one embodiment, the therapy apparatus 110 is characterized in that it comprises cooling means 130 allowing cooling to be performed in a predetermined temperature range, of at least the tissue region 114 situated at the interface with therapy device 116, providing effective protection of the tissue zones at said interface 114.

Advantageously, the cooling means 130 comprise a refrigerating fluid, 132, preferably a liquid refrigerating medium such as in particular, degassed water.

According to a further particularly advantageous embodiment, therapy device 116 is provided with a membrane in the form of a pocket or bag, fixed in a sealed manner onto treatment device 116, as will be readily understood by those skilled in the art from FIG. 8. This membrane, which is closed in a sealed manner, is completely filled with cooling liquid 132. Means 136 for circulating the cooling liquid are also provided for the purposes of renewing it, and for keeping it in the intended cooling temperature region. According to one special embodiment, the cooling means 130 also provide cooling of the piezoelectric transducer element 118, which is generally the case when membrane 134 externally surrounds at least the transducer element 118 so that the latter is immersed or is in permanent contact with cooling liquid 132.

The circulating means 136 comprise, for example, a conduit 138 for introducing cooling fluid from a constant temperature device 140 which includes at least one temperature regulation device 142 which controls a cooling unit 144, for example a heat exchanger, device 142 being coupled to one or several temperature sensors 146, 148 one of which, such as the one bearing the reference 146, being able to be disposed in the cooling liquid 132 and the other one, such as 148, being arranged externally to membrane 144, between the latter and the surface S of the skin of the mammal M. The cooling fluid leaves through a conduit 139 in order to return to cooling unit 144, optionally passing through a degassing device 150. Circulation pumps such as the one indicated by reference 152 can obviously be provided.

The complete cooling means are advantageously controlled by control unit 120.

Moreover, a pressure sensing device 154 also inserted externally between the membrane 134 and surface S of the skin of mammal M can also be provided, for transmitting pressure data over a corresponding conductor element 156 to control unit 120 so that the latter can modify the commands sent out to the control means 122.

According to the a particularly advantageous embodiment of the invention shown in FIG. 8, the therapy device 110 is extra-corporeal.

According to another embodiment, which is not shown, the therapy device can be an endocavitary device allowing semi-invasive therapy to be performed; this endocavitary device can in particular be an endo-urethral or an endo-rectal device. It can also be an endo-esophagal device. As the provision of such an endocavitary device is well known to those skilled in the art, it was considered not to be necessary to show this in the figures. Reference can also be made to U.S. Pat. Nos. 5,316,000 and 5,474,071.

The tissue temperature measuring devices such as 148 advantageously comprise sensors in thermocouple form, or in sheet form, particularly of the PVDF type which has the advantage of being able to be provided in extremely thin film form, and which can thus be disposed directly on the tissue regions of the interface, opposite the therapy device 116, or yet again, on the outer side of membrane 134 as shown, said membrane being applied against the surface S of interface tissue 114. Moreover, here, the sensor 154 which is advantageously in sheet form, particularly PVDF-sheet form enables measurement of the ultrasound acoustic pressure field delivered by therapy device 116 to be measured at interface 114 level, this making it possible to know, with considerable accuracy and moreover in real time, what the acoustic power in the focal region is.

Figure 9:
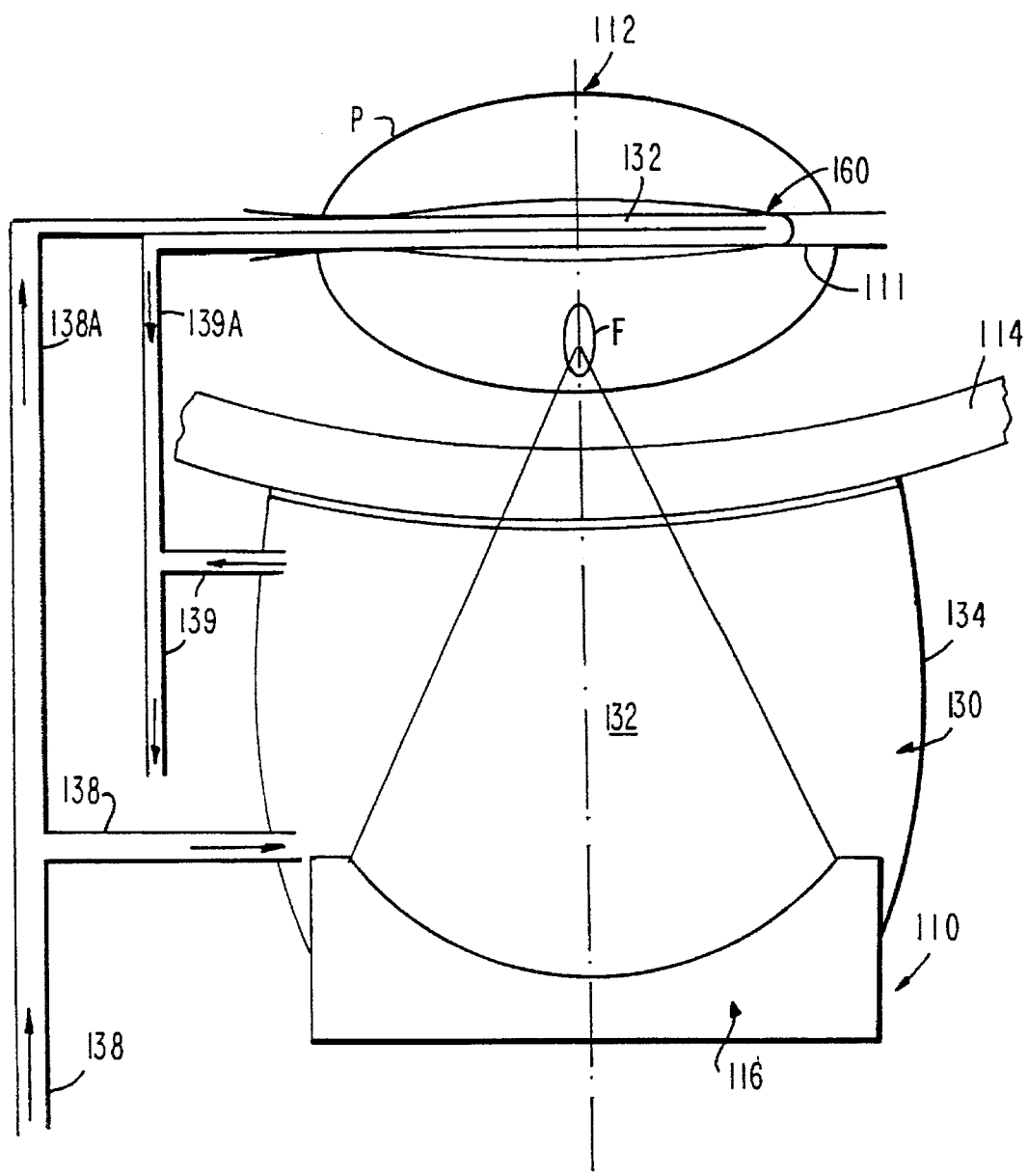
FIG. 9 shows an alternative embodiment of the apparatus in FIG. 8 including, additionally, an endo-cavitary cooling probe ensuring tissue regions remote from the therapy device are cooled.

Referring now to FIG. 9, an alternative embodiment of the apparatus in FIG. 8 has been shown, at least one endocavitary device 160 which is physically independent of therapy device 116 being provided, for the cooling of tissue regions that are remote from therapy device 116 and which it is also desired to protect during therapy. The said endocavitary device 160 is advantageously designed to receive the same cooling fluid 132 as the one use for therapy device 116. Here for treatment of the prostate P, the urethra U is shown diagrammatically, and endocavitary device 160 is an endo-urethral device. Endocavitary device 160 comprises a conduit 138A for supplying cooling fluid 132 which branches off conduit 138 in FIG. 8, and an evacuation conduit 139A branching off outlet conduit 139 in FIG. 8, this only representing an extremely minor modification of the overall apparatus.

It can also be arranged for the endocavitary probe 160 to be fitted with temperature measuring devices allowing the temperature urethra U has reached to be checked, thus introducing additional safely into treatment.

How the apparatus shown in FIGS. 8 and 9 operates will be immediately apparent to those skilled in the art, from the description above.

It should be pointed out, while on this matter, that it is preferred to use for the focused piezo-electric transducer element, a transducer element with an opening 1 and which operates at a frequency of 1 MHz. For this type of transducer element, the volume of focal region F will typically be of elliptical shape, as illustrated, the major axis being 10 mm long and the minor axis 2 mm.

Here, it will be noticed that the volume of focal region F is very small compared to the size of prostate P, the latter defining the total volume of the tissue region that is to be treated by ultrasound therapy.

Bearing in mind that the volume of focal region F is very small compared to the total volume of the tissue to be treated, it suffices to displace treatment device 116 during treatment in order to achieve so-called point-by-point treatment covering the whole of the volume of the lesion to be treated.

It will be understood that in the case of particularly intense heat being created within focal volume F, heat energy spreads through tissue that may extend well beyond that of the lesion to be destroyed, invading, in particular, the tissue region that is to be preserved such as tissue region 114. This particularly applies when the focal volume F is quite close to the tissue region to be preserved, such as region 114 in FIGS. 8 to 9.

Such protection is also ensured by cooling at least tissue region 114 (FIG. 8), and optionally the region U of the urethra in FIG. 9., thanks to the presence of membrane 134 situated in contact with the tissue 114, and, optionally, thanks to the presence of the supplementary endocavitary probe 160.

Membrane 134 is characterized by its transparency to the acoustic field, and its thermal conducting capacity. A suitable material is chosen to provide said characteristics, such as latex or silicone rubber. Membrane thickness in the region where the acoustic field passes is preferably reduced to a minimum. It can vary from several micrometers up to several millimeters, depending on the application envisaged (extracorporeal or endocavitary).

Thanks to the control provided by control unit 120 and temperature regulating device 140, cooling fluid 132 is cooled down to a predetermined temperature that is lower than the mammal's body temperature, and in particular is below 37° C., and even better below 35° C., and better still below 30° C. A particularly useful range of temperatures is that comprised between 4° C. and 30° C., and even better between 15° C. and 25° C.

It should be noted that in FIG. 8 the temperature and/or pressure sensors 148, 154 in the form of extremely thin sheet(s) are transparent to the acoustic field and do not in practice cause any interference. Given that these sensors are sensitive to pressure, they enable the acoustic field pressure'supplied by focused transducer element 118 to be measured. The pressure information is transmitted to the control unit 120 for commanding the control means 122, notably for varying the electrical power fed to the ultrasound acoustic transducer element.

It is obviously possible to apply an acoustic coupling compound, such as silicone grease, to the patient's skin when carrying out therapy.

A positioning device, such as device 40 in FIG. 1 can also be provided for accurately positioning the focal region F of focused transducer element 118 of FIG. 8 opposite the lesion to be destroyed.

The choice of how much ultrasound power to use depends on the depth of the lesion to be destroyed. Ultrasound power is controlled and regulated during successive shots by pressure sensing device 154.

In FIG. 8, as soon as shooting starts, temperature sensor 148 measures the temperature reached by the tissue that is to be preserved 114, which, in this case, is the patient's skin, for supply of the relevant information to temperature regulating device 136. The latter device acts on cooling unit 144 in order to keep the temperature of tissue to be preserved at a constant determined value, in order to avoid or limit cavitation effects resulting from the therapeutic high energy ultrasound acoustic waves employed. Regulation is achieved by reducing to a greater or smaller extent the temperature of cooling fluid 132, which preferably is a liquid such as degassed tap water.

It can thus be seen that the invention enables the determining technical advantages stated above to be achieved in a simple, safe and effective manner from the therapeutic point of view, and with considerable versatility ensuring ready adaptability to all types of lesions to be treated. The invention obviously covers all means that are technical equivalents of the means described as well as various combinations thereof.

Moreover, the invention covers all technical means that appear to be novel over any state of the art and which result from the preceding description in combination with the drawings which constitute an integral part thereof.

What is claimed is:

1. A therapy method using ultrasound for the purpose of destroying a target to be destroyed, said target including tissue which may be located inside a body of a mammal, by supplying ultrasonic waves focused onto a focal point or region F determining a tissue zone to be submitted to said therapy, which comprises supplying ultrasonic waves of two types, thermal waves, for producing a predominantly thermal effect on tissue to be treated, and cavitation waves, for producing a predominantly cavitation effect on said tissue to be treated, said two types of waves being applied for a time sufficient to effect therapy by destroying at least a portion of said tissue.

2. A therapy method using ultrasound for the purpose of destroying a target to be destroyed, said target including tissue which may be located inside a body of a mammal, by supplying ultrasonic waves focused onto a focal point or region F determining a tissue zone to be submitted to said therapy, which comprises supplying ultrasonic waves of two types, thermal waves, for producing a predominantly thermal effect on tissue to be treated, and cavitation waves, for producing a predominantly cavitation effect on said tissue to be treated, said two types of waves being applied for a time sufficient to effect therapy by destroying at least a portion of said tissue and wherein said thermal ultrasonic waves are supplied at least at a beginning of treatment.

3. The method according to claim 2, wherein said cavitation ultrasonic waves are supplied after an adjustable predetermined time interval for allowing preheating of the tissue to be treated.

4. The method according to claim 3, wherein said cavitation ultrasonic waves are supplied simultaneously with said thermal ultrasonic waves.

5. The method according to claim 3, wherein acoustic power of said thermal ultrasonic waves is lower than a cavitation threshold whereas acoustic power of said cavitation ultrasonic waves is at least equal to the cavitation threshold, said cavitation threshold being a function of the tissue of the mammal to be treated.

6. The method according to claim 3, wherein the frequency of said cavitation ultrasonic waves is lower than the frequency of said thermal ultrasonic waves.

7. The method according to claim 3, wherein said cavitation ultrasound waves include a negative amplitude component of a nature to initiate cavitation.

8. The method according to claim 3, wherein said cavitation ultrasound waves are supplied for a duration of between about 0.5 microseconds and about 100 milliseconds.

9. The method according to claim 3, wherein said cavitation ultrasound waves are supplied by successive pulses, repetition frequency of which varies from about 1 Hz to about 1 KHz.

10. The method according to claim 3, wherein the duration of said adjustable predetermined time interval is between about 100 milliseconds and about 10 seconds.

11. The method according to claim 3, wherein the total duration of treatment of the tissue region determined by the focal point or region F by means of the said ultrasound waves is between about 100 milliseconds and 10 seconds, this total duration including at least one pulse of cavitation ultrasound waves.

12. The method according to claim 3, wherein the frequency of transmission of said cavitation ultrasound waves is between about 500 KHz and about 4 MHz.

13. The method according to claim 3, wherein the frequency of transmission of said thermal ultrasound waves is between about I 1 and about 4 MHz, said frequency being at least equal to the frequency being at least equal to the frequency of said cavitation ultrasound waves.

14. The method according to claim 3, wherein the acoustic power of said thermal ultrasound waves is lower than about 150 W/cm$^2$, and the acoustic power of said cavitation ultrasound waves is at least equal to about 150 W/cm$^2$.

15. The method according to claim 3, further comprising the step of providing transmission of ultrasound waves of an amplitude that varies as a function of time, said amplitude preferably increasing with the passage of time, whereby the amplitude over a first period remains below a cavitation threshold, then, in a second period becomes higher than said cavitation threshold.

16. The method according to claim 30, further comprising the step of displacing said focal point to perform point-by-point treatment, each of said points being determined by the said focal point or region F, in order to cover the entire volume of the tissue target to be treated.

17. A therapy method using ultrasound for the purpose of destroying a target to be destroyed, said target including tissue which may be located inside a body of a mammal, by supplying ultrasonic waves focused onto a focal point or region F determining a tissue zone to be submitted to said therapy, which comprises supplying ultrasonic waves of two types, thermal waves, for producing a predominantly thermal effect on tissue to be treated, and cavitation waves, for producing a predominantly cavitation effect on said tissue to be treated, said two types of waves being applied for a time sufficient to effect therapy by destroying at least a portion of said tissue, displacing said focal point to perform point-by-point treatment, each of said points being determined by the said focal point or region F, in order to cover the entire volume of the tissue target to be treated, and conducting an imaging step to acquire volume data so that said focal point may be displaced as a function of the volume of the target to be treated.

18. The method according to claim 17, further comprising the step of displacing the focal point in order to carry out treatment of the tissue regions of said target which are most remote from said ultrasonic waves up to the tissue regions that are closest to said ultrasonic waves so as to improve effectiveness of treatment of said target.

19. The method according to claim 17, further comprising the step of displacing the focal point with a latency period between treatment of two successive points on the target to be treated in order to allow said tissue being treated to relax, said latency period being between about 1 second and 15 seconds and being employed for carrying out displacement of the focal point from one treatment point to another.

20. The method according to claim 17, further comprising the step of displacing the focal point in a random manner while excluding points that have already been treated.

21. An apparatus for performing therapy using ultrasound, comprising at least one treatment device comprising at least one piezoelectric transducer element designed to provide at least said therapy for the purpose of destroying a target to be destroyed, said target including tissue which may be located inside a body of a mammal, and control means for said device in order to carry out said therapy, said piezoelectric transducer element being designed to supply ultrasonic waves focused onto a focal point or region F determining the tissue zone to be submitted to said therapy, said apparatus further comprising control means for causing said treatment device to supply ultrasonic waves of two types, thermal waves, for producing a predominantly thermal effect on the tissues to be treated, and cavitation waves, for producing a predominantly cavitation effect on said tissues to be treated when such tissues are exposed to said two types of ultrasonic waves.

22. An apparatus for performing therapy using ultrasound, comprising at least one treatment device comprising at least one piezoelectric transducer element designed to provide at least said therapy for the purpose of destroying a target to be destroyed, said target including tissue which may be located inside a body of a mammal, and control means for said device in order to carry out said therapy, said piezoelectric transducer element being designed to supply ultrasonic waves focused onto a focal point or region F determining the tissue zone to be submitted to said therapy, said apparatus further comprising control means for causing said treatment device to supply ultrasonic waves of two types, thermal waves, for producing a predominantly thermal effect on the tissues to be treated, and cavitation waves, for producing a predominantly cavitation effect on said tissues to be treated when such tissues are exposed to said two types of ultrasonic waves, wherein said control means causes said treatment device to transmit thermal ultrasonic waves at least at the beginning of said treatment.

23. The apparatus according to claim 22, wherein said control means cause said treatment device to transmit cavitation ultrasonic waves after an adjustable predetermined time interval allowing pre-heating of the tissue to be treated.

24. The apparatus according to claim 23, wherein said control means causes the transmission of cavitation ultrasonic waves simultaneously with the transmission of thermal ultrasonic waves.

25. The apparatus according to claim 23, wherein acoustic power of said thermal ultrasonic waves is lower than a cavitation threshold whereas acoustic power of said cavitation ultrasonic waves is at least equal to the cavitation threshold, said cavitation threshold being a function of the tissue of the mammal to be treated.

26. The apparatus according to claim 23, wherein a frequency of said cavitation ultrasonic waves is lower than a frequency of said thermal ultrasonic waves.

27. The apparatus according to claim 23, wherein said control means causes transmission of cavitation ultrasound waves including a negative component of the amplitude thereof of a nature to initiate cavitation.

28. The apparatus according to claim 23, wherein said control means causes transmission of cavitation ultrasound waves for a duration of between about 0.5 microseconds and about 100 milliseconds.

29. The apparatus according to claim 23, wherein said control means provides transmission of cavitation ultrasound waves by successive pulses, the repetition frequency of which varies from about 1 Hz to about 1 KHz.

30. The apparatus according to claim 23, wherein the duration of said adjustable predetermined time interval is between about 100 milliseconds and about 10 seconds.

31. The apparatus according to claim 23, wherein the total duration of treatment of the tissue region determined by the focal point or region F by means of the said ultrasound waves is between 100 milliseconds and 10 seconds, this total duration including at least one pulse of cavitation ultrasound waves.

32. The apparatus according to claim 23, wherein frequency of transmission of said cavitation ultrasound waves is between about 500 KHz and about 4 MHz.

33. The apparatus according to claim 23, wherein frequency of transmission of said thermal ultrasound waves is between about 1 and about 4 MHz, said frequency being at least equal to the frequency of said cavitation ultrasound waves.

34. The apparatus according to claim 23, wherein acoustic power of said thermal ultrasound waves is lower than 150 W/cm$^2$, and the acoustic power of said cavitation ultrasound waves is at least equal to about 150 W/cm$^2$.

35. The apparatus according to claim 23, wherein said control means provides transmission of ultrasound waves of an amplitude that varies as a function of time, said amplitude preferably increasing with the passage of time, whereby the amplitude over a first period remains below a cavitation threshold, then, in a second period becomes higher than said cavitation threshold.

36. The apparatus according to claim 22, comprising means for displacing said treatment device in order to perform point-by-point treatment, each of said points being determined by the said focal point or region F, in order to cover the entire volume of the target to be treated.

37. An apparatus for performing therapy using ultrasound, comprising at least one treatment device comprising at least one piezoelectric transducer element designed to provide at least said therapy for the purpose of destroying a target to be destroyed, said target including tissue which may be located inside a body of a mammal, and control means for said device in order to carry out said therapy, said piezoelectric transducer element being designed to supply ultrasonic waves focused onto a focal point or region F determining the tissue zone to be submitted to said therapy, said apparatus further comprising control means for causing said treatment device to supply ultrasonic waves of two types, thermal waves, for producing a predominantly thermal effect on the tissues to be treated, and cavitation waves, for producing a predominantly cavitation effect on said tissues to be treated when such tissues are exposed to said two types of ultrasonic waves and means for displacing said treatment device in order to perform point-by-point treatment, each of said points being determined by the said focal point or region F, in order to cover the entire volume of the target to be treated, wherein said displacement means of the treatment device are controlled by a control unit which includes a computer or micro-computer, the latter being provided with software managing displacement of said treatment device as a function of the volume of the target to be treated, volume data having advantageously been acquired by imaging means associated therewith having special imaging control means controlled by said control unit for translatory or rotational displacement.

38. The apparatus according to claim 37, wherein said control unit controls the displacement of said displacement means of said treatment device in order to carry out treatment of the tissue regions of said target which are most remote from said treatment device up to the tissue regions that are closest to said treatment device in order to improve the effectiveness of treatment of said target.

39. The apparatus according to claim 37, wherein said control means provides a latency period between treatment of two successive points on the target to be treated in order to allow said tissue being treated to relax, said latency period being between about 1 second and 15 seconds, said latency period being employed for carrying out displacement of the treatment device from one treatment point to another.

40. The apparatus according to claim 37, wherein said control unit controls displacement of said displacement means of said treatment device in a random manner while excluding points that have already been treated.

* * * * *